(12) United States Patent
Loboda

(10) Patent No.: US 9,952,132 B2
(45) Date of Patent: *Apr. 24, 2018

(54) SAMPLE ANALYSIS FOR MASS CYTOMETRY

(71) Applicant: Fluidigm Canada Inc., Markham (CA)

(72) Inventor: Alexandre Loboda, Thornhill (CA)

(73) Assignee: Fluidigm Canada Inc., Markham (CA)

(*) Notice: Subject to any disclaimer, the term of this patent is extended or adjusted under 35 U.S.C. 154(b) by 0 days.

This patent is subject to a terminal disclaimer.

(21) Appl. No.: 15/408,806

(22) Filed: Jan. 18, 2017

(65) Prior Publication Data

US 2017/0248507 A1 Aug. 31, 2017

Related U.S. Application Data

(63) Continuation of application No. 14/783,791, filed as application No. PCT/CA2014/050387 on Apr. 17, 2014, now Pat. No. 9,589,779.

(60) Provisional application No. 61/812,893, filed on Apr. 17, 2013.

(51) Int. Cl.
| | |
|---|---|
| *G01N 15/10* | (2006.01) |
| *H01J 49/04* | (2006.01) |
| *H01J 49/10* | (2006.01) |
| *G01N 15/00* | (2006.01) |
| *H01J 49/40* | (2006.01) |

(52) U.S. Cl.
CPC ......... *G01N 15/10* (2013.01); *H01J 49/0463* (2013.01); *H01J 49/105* (2013.01); *G01N 2015/0065* (2013.01); *G01N 2015/1006* (2013.01); *H01J 49/40* (2013.01)

(58) Field of Classification Search
USPC .......................................... 250/288, 281, 282
See application file for complete search history.

(56) References Cited

U.S. PATENT DOCUMENTS

| | | | |
|---|---|---|---|
| 4,740,692 | A | 4/1988 | Yamamoto et al. |
| 5,294,797 | A | 3/1994 | Frey et al. |
| 6,111,251 | A | 8/2000 | Hillenkamp |
| 7,180,058 | B1 | 2/2007 | Izgarian et al. |
| 8,598,488 | B2 | 12/2013 | O'Connor et al. |
| 8,879,064 | B2 | 11/2014 | O'Connor et al. |

(Continued)

FOREIGN PATENT DOCUMENTS

| | | |
|---|---|---|
| CN | 105324832 | 2/2016 |
| DE | 102008049833 | 4/2010 |

(Continued)

OTHER PUBLICATIONS

Batsala et al., "Inductively Coupled Plasma Mass Spectrometry (ICP-MS)", Res. Pharm. and Chem, vol. 2, No. 3, 2012, pp. 671-680.
Becker et al., "Imaging of metals and metal-containing species in biological tissues and on gels by laser ablation inductively coupled plasma mass spectrometry (LA-ICP-MS): A new analytical strategy for applications in life sciences*", Pure Appl. Chem., vol. 80, No. 12, 2008, pp. 2643-2655.

(Continued)

*Primary Examiner* — Kiet T Nguyen
(74) *Attorney, Agent, or Firm* — Kilpatrick Townsend & Stockton LLP

(57) ABSTRACT

The invention relates to methods and devices for analysis of samples using laser ablation inductively coupled plasma mass spectrometry (LA-ICP-MS). The invention provides methods and devices in which individual ablation plumes are distinctively captured and transferred to the ICP, followed by analysis by mass cytometry.

20 Claims, 10 Drawing Sheets

Ablation from the top, sampling through a cone

(56) References Cited

U.S. PATENT DOCUMENTS

| | | | |
|---|---|---|---|
| 9,383,260 B1* | 7/2016 | Yoo | B23K 26/032 |
| 2010/0213367 A1 | 8/2010 | Miller et al. | |
| 2012/0061561 A1 | 3/2012 | Antonov et al. | |
| 2012/0074307 A1 | 3/2012 | Becker et al. | |
| 2012/0099103 A1 | 4/2012 | Hahn et al. | |
| 2014/0287953 A1 | 9/2014 | Günther et al. | |
| 2015/0165550 A1 | 6/2015 | Fry et al. | |
| 2016/0056031 A1 | 2/2016 | Loboda | |

FOREIGN PATENT DOCUMENTS

| | | |
|---|---|---|
| EP | 1084505 | 7/2008 |
| WO | 2008080224 | 7/2008 |

OTHER PUBLICATIONS

Becker et al., "Laser ablation inductively coupled plasma mass spectrometry (LA-ICP-MS) in elemental imaging of biological tissues and in proteomics", Journal of Analytical Atomic Spectometry, vol. 22, Jun. 2007, pp. 736-744.

Giesen et al., "Multiplexed Immunohistochemical Detection of Tumor Markers in Breast Cancer Tissue Using Laser Ablation Inductively Coupled Plasma Mass Spectrometry", Anal. Chem., vol. 83 (21),, Sep. 18, 2011, pp. 8177-8183.

PCT/CA2014/050387, "International Search Report", dated Jul. 15, 2014, 4 pages.

EP14784995.4, "European Search Report and Written Opinion", dated Oct. 27, 2016, 9 pages.

\* cited by examiner

SAMPLE ANALYSIS FOR MASS CYTOMETRY

CROSS-REFERENCE TO RELATED APPLICATIONS

This application is continuation of U.S. patent application Ser. No. 14/783,791, filed on Oct. 9, 2015, which is a US National Phase of PCT Application No. PCT/CA2014/050387, filed on Apr. 17, 2014, which claims benefit of U.S. Provisional application No. 61/812,893, filed Apr. 17, 2013, the entire contents of which are incorporated herein by reference

TECHNICAL FIELD

This invention relates to apparatus and methods for laser ablation for cellular analysis by mass cytometry.

BACKGROUND OF THE INVENTION

Laser ablation combined with inductively coupled plasma mass spectrometry (ICP-MS) can be used for imaging of biological samples (cells, tissues, etc.) labeled with elemental tags. Each laser pulse generates a plume of ablated material from the sample which can be transferred to be ionized for further analysis by the mass analyzer. The information acquired from the laser pulses at each location on the sample can then be used for imaging the sample based on its analyzed content. However, this technique has limitations in its ability to separately resolve each discrete plume of ablated material produced from each laser ablation pulse on the sample.

BRIEF SUMMARY OF THE INVENTION

In one aspect the invention provides a method of laser ablation mass cytometry analysis comprising: directing pulses of a laser beam to a sample for generating a plume of sample for each of the pulses; capturing each plumes distinctively for each of the pulses; transferring the distinctively captured plume to an ICP; and ionizing the distinctively captured and transferred plumes in the ICP and generating ions for mass cytometry analysis.

In a related aspect the invention provides a laser ablation mass cytometer comprising: a laser ablation source for generating an ablated plume from a sample and an injector adapted to couple the laser ablation source with an ICP of the mass cytometer; the injector having an inlet positioned within the laser ablation source, the inlet being configured for capturing the ablated plume as the ablated plume is generated; and a gas inlet coupled to the inlet of the injector for passing a gas there between for transferring the captured ablated plume into the ICP.

Also disclosed, for illustration and not limitation, are the following exemplary aspects of the invention.

Aspect 1. A method of laser ablation mass cytometry analysis using a laser ablation mass cytometer is disclosed, the method comprising: a) directing pulses of a laser beam to a plurality of sites of a sample for generating an ablated plume of sample for each of the pulses; b) capturing each ablated plume distinctively; c) transferring each of the distinctively captured ablated plumes to an inductively coupled plasma (ICP); and d) ionizing each of the distinctively captured and transferred ablated plumes in the ICP, thereby generating ions for mass cytometry analysis.

Aspect 2. The method of aspect 1, wherein the laser ablation mass cytometer comprises: a laser ablation source for generating ablated plumes from a sample; an ICP source for producing the ICP; and an injector adapted to transfer the ablated plumes to the ICP; the injector having an injector inlet positioned within the laser ablation source, the injector inlet being configured for capturing the ablated plumes; and a gas inlet coupled to the injector inlet configured to pass a gas from the gas inlet to the injector inlet for transferring the captured ablated plume into the ICP.

Aspect 3. The method of aspect 2 wherein the injector inlet is configured for capturing all or part of the ablated plume as the ablated plume is generated.

Aspect 4. The method of any of aspects 1-3 wherein the ablated plume is generated by a laser pulse that is directed at a target comprising a sample disposed on a substrate.

Aspect 5. The method of any of aspects 1-3 wherein the ablated plume is generated by a laser pulse that is directed through a transparent target comprising the sample.

Aspect 6. The method of aspect 5 wherein the transparent target comprises a transparent substrate on which the sample is situated.

Aspect 7. The method of any of aspects 2-6 wherein the injector inlet has the form of a sample cone, wherein the narrower portion of the cone is the aperture of the injector inlet.

Aspect 8. The method of aspect 7 wherein the sample cone is positioned near the area where the ablated plume is generated.

Aspect 9. The method of aspect 8 wherein the sample cone is positioned about 100 microns away from the surface of the target surface.

Aspect 10. The method of any of aspects 7-9 wherein the diameter of the aperture a) is adjustable; b) is sized to prevent perturbation to the ablated plume as it passes into the injector; and/or c) is about the equal to the cross-sectional diameter of the ablated plume.

Aspect 11. The method of aspect 7 wherein the diameter of the aperture is about 100 microns.

Aspect 12. The method of any of aspects 4-12 further comprising introducing a gas flow into the region between the injector inlet and the target, to aid in directing the plume through the injector inlet.

Aspect 13. The method of aspect 12 wherein the gas flow is transverse to the target and is transverse to the centerline of the injector lumen, at least in the portion of the lumen proximal to the injector inlet.

Aspect 14. The method of aspect 12 or 13 wherein the target is a transparent target.

Aspect 15. The method of any of aspects 12-14 wherein the gas flow comprises argon.

Aspect 16. The method of any of aspects 12-15 further comprising introducing a transfer gas flow into the injector for transferring the plume toward the ICP.

Aspect 17. The method of aspect 16 wherein the gas flow is about 0.1 liters per minute and the transfer flow is about 0.9 liters per minute.

Aspect 18. The method of aspects 16 or 17 wherein the transfer flow comprises argon.

Aspect 19. The method of any of aspects 1-4, 7-13, or 15-18 wherein the sample is on a substrate and the ablated plume is generated by a laser pulse that is directed to the sample from the same side as the sample.

Aspect 20. The method of any of aspects 2-19, wherein the gas inlet is configured to direct a power wash gas flow near the zone where the ablated plume is formed, to direct the ablated plume towards the injector inlet.

Aspect 21. The method of aspect 20, wherein the gas inlet comprises a nozzle having an aperture smaller than the diameter of the injector inlet.

Aspect 22. The method of any of aspects 1-21 wherein the laser beam is from a femtosecond laser.

Aspect 23. The method of aspect 1 wherein the ablated plume is generated by a laser pulse that is directed through a transparent target comprising a transparent substrate and the sample.

Aspect 24. The method of aspect 23 wherein the laser ablation mass cytometer comprises: a laser for generating ablated plumes from a sample; an inductively coupled plasma (ICP) torch; an injector adapted to transfer ablated plumes to an ICP produced by the ICP torch; wherein the injector comprises a wall and a lumen and a portion of the injector wall is comprised of the transparent substrate; wherein the injector comprises an injector inlet for introducing a gas flow into the lumen flowing, and wherein the transparent substrate is located between the injector inlet and the ICP torch; the sample is attached to the lumen side of the transparent substrate; the ablated plumes are formed in an orientation transverse to the injector lumen and are formed entirely in the injector lumen; and each ablated plume is distinctly captured by gas flowing through the injector lumen toward the ICP.

Aspect 25. The method of aspect 24 wherein the position of the target is fixed during analysis.

Aspect 26. The method of aspect 25 wherein directing pulses of a laser beam to a plurality of sites of a sample comprising moving the laser beam to sites of interest across a stationary sample.

Aspect 27. The method of aspect 26 wherein the laser beam is moved in a raster pattern for imaging.

Aspect 28. The method of aspect 24 wherein the position of the target is changed during analysis.

Aspect 29. The method of aspect 28 wherein, during analysis, the laser beam remains stationary and the target is moved.

Aspect 30. The method of any of aspects 4-29 in which the position of the target is fixed during analysis.

Aspect 31. The method of aspect 30 wherein, during analysis, the laser beam remains stationary and the target is moved.

Aspect 32. The method of any of aspects 4-29 in which the position of the target is moved during analysis.

Aspect 33. The method of any of aspects 1-32 wherein the laser beam pulses produce 1 micron ablation spots.

Aspect 34. The method of any preceding aspect wherein the cross-sectional diameter of the ablated plume is on the scale of 100 microns.

Aspect 35. The method of any preceding aspect wherein the injector is a tube with an approximately 1 mm inner diameter.

Aspect 36. The method of any preceding aspect wherein the ablated plumes formed by each laser pulse comprise sample particles with dimensions of about 1 µm or less.

Aspect 37. The method of any of preceding aspect wherein spreading of the ablation plume as it is transferred to the ICP is maintained within the internal diameter of the injector lumen.

Aspect 38. A laser ablation mass cytometer comprising: a laser ablation source for generating ablated plumes from a sample; a laser that emits a laser beam from a surface, the surface oriented to direct the beam to a sample contained in the laser ablation source; an inductively coupled plasma (ICP) torch; an injector adapted to couple the laser ablation source with an ICP produced by the ICP torch; the injector having an injector inlet positioned within the laser ablation source, the injector inlet being configured for capturing the ablated plume as the ablated plume is generated; and a gas inlet coupled to the injector inlet of the injector inlet configured to pass a gas from the gas inlet to the injector inlet for transferring the captured ablated plume into the ICP.

Aspect 39. The cytometer of aspect 38 configured so that the laser beam is oriented directly toward the opening of the injector inlet.

Aspect 40. The cytometer of aspect 39 configured so that the laser beam is aligned with the lumen of the injector at least at the portion of the lumen proximal to the injector inlet.

Aspect 41. The cytometer of aspect 39 configured so that a projection of the laser beam is transverse to the centerline of the injector lumen, at least in the portion of the lumen proximal to the injector inlet.

Aspect 42. The cytometer of any of aspects 38-41 wherein the laser ablation source is adapted to receive a transparent target.

Aspect 43. The cytometer of aspect 42 further comprising a transparent target.

Aspect 44. The cytometer of aspects 42 or 43 wherein the transparent target comprises a transparent substrate and the sample.

Aspect 45. The cytometer of any of aspects 38-44 wherein the diameter of the aperture of the injector inlet is less than the inner diameter of the injector.

Aspect 46. The cytometer of any of aspects 38-44 wherein the injector inlet has the form of a sample cone.

Aspect 47. The cytometer of aspect 46 wherein the sample cone is positioned near the zone where ablation plumes are generated.

Aspect 48. The cytometer of aspect 46 wherein the diameter of the aperture is adjustable.

Aspect 49. The cytometer of any of aspects 45-48 comprising a transparent target.

Aspect 50. The cytometer of any of aspects 38-49 further comprising a gas flow inlet configured to direct gas in an orientation transverse to the centerline of the lumen of the injector at least at the portion of the lumen proximal to the injector inlet.

Aspect 51. The cytometer of any of aspects 38-50 further comprising a gas flow inlet configured to direct gas across the surface of the transparent target toward the aperture, to aid in directing an ablation plume through the injector inlet.

Aspect 52. The cytometer of aspect 51, wherein the injector inlet has the form of a sample cone, further comprising a transfer gas flow inlet positioned configured to direct gas into the lumen of the injector.

Aspect 53. The cytometer of aspect 38 comprising a power wash gas inlet configured to direct ablated plumes into the injector inlet.

Aspect 54. The cytometer of aspect 53 wherein the power wash gas inlet comprises a nozzle having an aperture smaller than the aperture of the injector inlet.

Aspect 55. A laser ablation mass cytometer comprising: a femtosecond laser for generating ablated plumes from a sample; an inductively coupled plasma (ICP) torch; an injector adapted to transfer ablated plumes to an ICP produced by the ICP torch; wherein the injector comprises a wall and a lumen, and a portion of the injector wall is comprised of the transparent substrate, said transparent substrate adapted to receive the sample; wherein the injector comprises an injector inlet for introducing gas into the lumen, wherein the transparent substrate is located between the injector inlet and the ICP torch.

Aspect 56. The cytometer of aspect 55 wherein the transparent substrate is movable relative to other portions of the injector wall.

Aspect 57. The cytometer of aspect 56 wherein the transparent substrate can be moved in a raster pattern relative to other portions of the injector wall.

Aspect 58. A laser ablation system comprising a) a laser capable of producing laser illumination; b) a laser ablation cell comprising a transparent substrate for holding a sample to be analyzed or a stage configured to receive a transparent substrate; and c) an injector for carrying an ablation plume to an ICP, said injector comprising an injector opening, wherein the (a), (b) and (c) are configured so that the laser illumination originates on one side of the stage or substrate and the injector opening is on the other side.

Aspect 59. The system of aspect 58 in which the laser illumination passed through an optical window into the ablation cell.

Aspect 60. The system of aspect 59 in which the injector opening is configured so that the ablation of an area of the substrate results in an ablated plume formed downstream of a surface from which the laser illumination is emitted.

Aspect 61. The system of aspect 60 in which the surface is a lens or mirror.

Aspect 62. The system of aspect 61 in which the injector opening is configured so that the ablation of an area of the substrate results in an ablated plume formed at least partially in the injector.

Aspect 63. The system of any of aspects 58-62 comprising (a) a transfer gas source for producing a transfer flow in the injector, (b) a capture gas source for producing a capture flow in the ablation cell, or both (a) and (b).

Aspect 64. The system of any of aspects 58-63 wherein the stage moves in x-y or x-y-z directions.

Aspect 65. The system of any of aspects 58-63 comprising a biological sample on the transparent substrate.

Aspect 66. The method of any of aspects 7-11 wherein the laser beam passes through said aperture.

Aspect 67. The method of aspect 66 in which the ablation plume expands towards the surface from which the laser beam emanates.

Aspect 68. A laser ablation inductively coupled plasma mass spectrometry system comprising: a laser ablation source for generating an ablated plume from a sample; a laser that emits a laser beam, wherein said beam passes through an objective lens to a sample contained in the laser ablation source; an inductively coupled plasma (ICP) torch; and, an injector adapted to couple the laser ablation source with an ICP produced by the ICP torch; wherein the injector passes though an opening in the objective lens; the injector having an injector inlet positioned within the laser ablation source, the injector inlet being configured for capturing the ablated plume as the ablated plume is generated.

Aspect 69. The system of aspect 68 wherein the laser beam is reflected from a mirror to the objective lens.

Aspect 70. The system of aspect 69 wherein the injector passes through an opening in the mirror.

Aspect 71. The system of any of aspects 68-70 wherein the ablation source comprises an inlet for a capture gas flow.

Aspect 72. The system of any of aspects 68-71 wherein the ablation source comprises a stage configured to receive a target.

Aspect 73. A laser ablation inductively coupled plasma mass spectrometry system configured for use according to any method disclosed herein.

BRIEF DESCRIPTION OF THE DRAWINGS

The skilled person in the art will understand that the drawings, described below, are for illustration purposes only. The drawings are not intended to limit the scope of the applicant's teachings in any way.

DETAILED DESCRIPTION OF VARIOUS EMBODIMENTS

Figure 1:
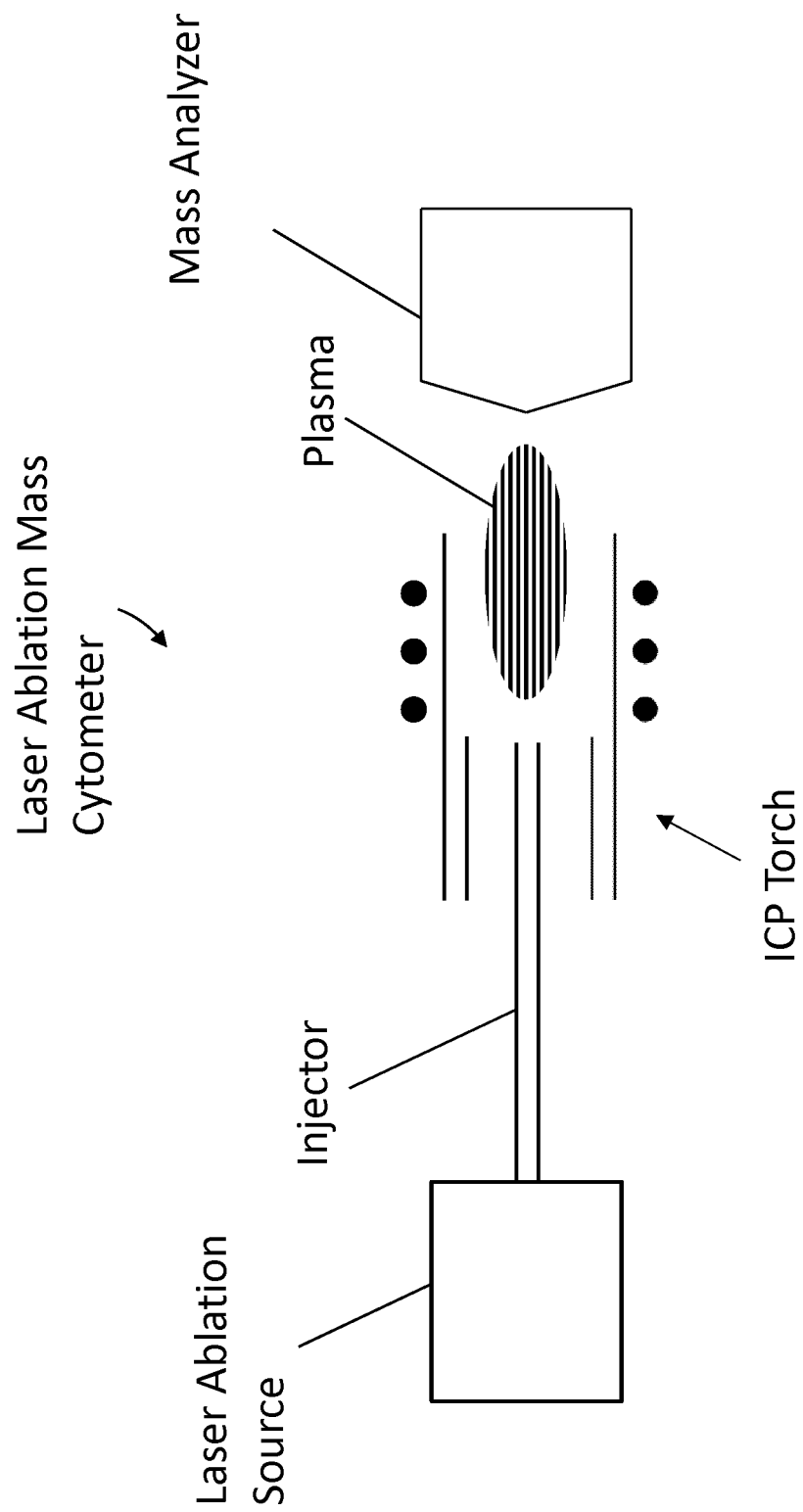
FIG. 1 is a schematic view of a laser ablation mass cytometer.

It should be understood that the phrase "a" or "an" used in conjunction with the present teachings with reference to various elements encompasses "one or more" or "at least one" unless the context clearly indicates otherwise.

The present invention relates to laser ablation combined with inductively coupled plasma mass spectrometry (LA-ICP-MS). LA-ICP-MS has been described for measurement of endogenous elements in biological materials and, more recently, for imaging by detection of elemental-tagged antibodies. See, e.g., Antonov, A. and Bandura, D., 2012, U.S. Pat. Pub. 2012/0061561, incorporated by reference herein; Seuma et al., "Combination of immunohistochemistry and laser ablation ICP mass spectrometry for imaging of cancer biomarkers" 2008, Proteomics 8:3775-3784; Hutchinson et al. "Imaging and spatial distribution of β-amyloid peptide and metal ions in Alzheimer's plaques by laser ablation—inductively coupled plasma-mass spectrometry" Analytical biochemistry 2005, 346.2:225-233; Becker et al. "Laser ablation inductively coupled plasma mass spectrometry (LA-ICP-MS) in elemental imaging of biological tissues and in proteomics." 2007, Journal of Analytical Atomic Spectrometry 22.7:736-744; Binet, et al., "Detection and characterization of zinc- and cadmium-binding proteins in *Escherichia coli* by gel electrophoresis and laser ablation-inductively coupled plasma-mass spectrometry" Analytical Biochemistry 2003, 318:30-38; Quinn, et al., "Simultaneous determination of proteins using an element-tagged immunoassay coupled with ICP-MS detection Journal of Analytical Atomic Spectrometry" 2002, 17:892-96; Sharma, et al., "*Sesbania drummondii* cell cultures: ICP-MS determination of the accumulation of Pb and Cu Microchemical Journal" 2005, 81:163-69; and Giesen et al. "Multiplexed immunohistochemical detection of tumor markers in breast cancer tissue using laser ablation inductively coupled plasma mass spectrometry" 2011, Anal. Chem. 83:8177-8183, each of which is incorporated by reference herein.

The present invention provides methods of laser ablation mass cytometry analysis in which pulses of a laser beam are directed to a sample for generating a plume of sample for each of the pulses; capturing each plume distinctively for each of the pulses; transferring each of the distinctively captured plume to an ICP; and ionizing each of the distinctively captured and transferred plumes in the ICP and generating ions for mass cytometry analysis and devices for carrying out the method. In various embodiments, a laser ablation mass cytometer can have a laser ablation source for generating an ablated plume from a sample and an injector adapted to couple the laser ablation source with an ICP of the mass cytometer. In some embodiments the injector can have an inlet positioned within the laser ablation source such that the inlet can be configured for capturing the ablated plume as the ablated plume is generated. A gas inlet can be coupled to the inlet of the injector for passing a gas there between for transferring the captured ablated plume into the ICP.

In one aspect the invention provides a laser ablation mass cytometer that has (i) a laser ablation source (ii) an injector adapted to couple the laser ablation source with an ICP produced by an ICP source; and (iii) a mass analyzer.

The laser ablation source, also referred to as the "ablation cell," houses the sample during ablation. Typically the ablation cell includes a laser transparent window to allow laser energy to strike the sample. Optionally the ablation cell includes a stage to hold the sample to be analyzed. In some embodiments the stage is movable x-y or x-y-z dimensions. In drawings and examples herein, the laser ablation source is sometimes shown as an open arrangement. However, such configurations are for illustration only, and it will be recognized that some form of suitable enclosure for preventing contamination or infiltration from the ambient environment is present. For example, a chamber configured with gas inlets and/or optical ports can be arranged around the laser ablation source to provide an enclosed environment suitable for capturing and transferring the ablated plume for ICP mass analysis. The gas inlets and optical port(s) are positioned so that the orientation of the laser beam, sample, plume expansion, and injector are suitable for the methods and devices disclosed herein. It will be appreciated that the ablation cell is generally gas tight (except for designed exits and ports).

Lasers used for laser ablation according to the invention generally fall into three categories: femtosecond pulsed lasers, deep UV pulsed lasers and pulsed lasers with a wavelength chosen for high absorption in the ablated material ("wavelength selective lasers"). Deep UV and wavelength specific lasers would likely operate with nanosecond or picosecond pulses. Each class of lasers has its drawbacks and benefits and can be chosen based on a particular application. In some embodiments, the laser is a femtosecond pulsed laser configured to operate with a pulse rate between 10 and 10000 Hz. Femtosecond laser are known (see, e.g., Jhanis et al., "Rapid bulk analysis using femtosecond laser ablation inductively coupled plasma time-of-flight mass spectrometry" J. Anal. At. Spectrom., 2012, 27:1405-1412.

Femtosecond lasers allow for laser ablation of virtually all materials with the only prerequisite for laser ablation being sufficient power density. This can be achieved even with relatively low pulse energy when the beam is tightly focused, for instance to 1 micrometer diameter and is short in duration (focused in time). Deep UV lasers also can ablate a large class of materials because most of the commonly used materials absorb deep UV photons. Wavelength selective laser ablation can utilize the lasers with the specific laser wavelength targeting absorption in the substrate material. A benefit of the wavelength specific laser may be the cost and simplicity of the laser and the optical system, albeit with a more limited spectrum of substrate materials. Suitable lasers can have different operating principles such as, for example, solid state (for instance a Nd:YAG laser), excimer lasers, fiber lasers, and OPO lasers.

A useful property of the femtosecond laser light is that it is absorbed only where the threshold power density is reached. Thus, a converging femtosecond laser light can pass through a thicker section of material without being absorbed or causing any damage and yet ablate the same material right at the surface where the focus is occurring. The focus can then be moved inside the material progressively as the sample layers are ablated. Nanosecond laser pulses might be partially absorbed by the substrate but can still work for ablation since the energy density at the focal point will be the highest (as long as it is sufficient for ablation).

The laser pulse may be shaped using an aperture, homogenized (if required) using a beam homogenizer, focused, e.g., using an objective lens, to produce a desired spot size less than 10 µm. Exemplary spot sizes include diameters (or equivalent sized ablation areas of other shapes) in the range of 0.10-3 µm (e.g., about 0.3 µm), 1-5 µm (e.g., about 3 µm), 1-10 µm (e.g., about 1, about 2, about 3, about 4 or about 5 µm), less than 10 µm, and less than 5 µm. In particular embodiments, a laser system is configured to operate with sufficiently focused laser pulses to ablate a sample area in the order of about 1 µm, e.g., 100 nm to 1 µm. Ablation on this small scale produces very small amount of plume material that in turn ensures that the size of the plume is kept small. A smaller plume is more likely to stay in the middle of the capture flow without contacting the walls of the ablation cell or of the injector gas conduits. Ablation on the 1 micrometer scale also means that the distance between the ablated surface and the area where plume expansion slows down and becomes dominated by the ambient gas is very short. This distance can range from a few micrometers to a few hundred micrometers. In some versions of the invention, the capture flow is present where the plume stops expanding. Therefore, for illustration and not limitation, several of the appended figures show the distance between the ablated surface and the region with capture flow shown as about 100 micrometers.

Although ablation on the 1 micrometer (or lower) scale is advantageous for certain applications (e.g., imaging), the methods and instruments of the invention are also useful when larger ablation spots are produced, such as ablation spots in the range of about 5 to about 35 microns diameter, for example in the range 5-15 microns, 10-20 microns, 15-25 microns, 20-30 microns and 25-35 microns. In some applications in which large ablation spots are produced, only a portion of the plume material is captured.

In some embodiments, the laser is situated outside the laser ablation source, and the laser beam (laser energy) enters the laser ablation source, e.g., though an optical window. As used herein, a laser beam may be describes as being emitted from a surface (e.g., a laser lens or mirror), which surface may be oriented to direct the beam to a particular location or pattern of locations. For ease of description of the invention, the directed beam may be considered to have a particular orientation; the orientation of the beam can refer to an imaginary line aligned with the beam and extending beyond the actual beam (for example when the beam strikes a non-transparent surface). As will be apparent from context, reference to the orientation or position of a laser beam sometimes refers to the orientation or position the beam of an unpowered laser source would produce if the laser was in use.

Mass analyzers for use in the invention may be selected based on the needs of the operator or specific application. Exemplary types of mass analyzers include quadrupole, time of flight, magnetic sector, high resolution, single or multi-collector based ICP mass spectrometers. Typically, time of flight mass spectrometers are used for the recording of fast transient events with the transit durations that are expected from the fast laser ablation ICP setup.

Ions are produced when particles of the ablation plume enter plasma (inductively coupled plasma, ICP) maintained within an ICP source or ICP torch.

A mass cytometer may be used for analysis or imaging of a biological sample, which may be on transparent substrate. In imaging embodiments, generally the laser may be operated with continuous train of pulses or in bursts of pulses directed to different positions of the sample, referred to as "spots of interest," or "locations or zones of ablation." The pulses may be directed to spots in a set pattern, such as a raster for two-dimensional imaging. Alternatively, a plurality of individual spots at different locations (for example, corresponding to individual cells) may be ablated. In some embodiments, the laser emits a burst of pulses producing a plume coming from the same pixel (i.e. the same location on the target). Ablation plumes produced by individual pulses within the burst are expected to fuse into one plume and travel within the instrument in such a way that they will be distinct from the plume produced from another pixel. To distinguish individual pixels, the time duration between bursts (pixel interrogation that can be just one pulse or 100 pulses) is maintained above a certain limit determined by the time spreading of the ion signal (at the detector) from an individual pixel.

As described below, one feature of the invention is that the ablation plume is transferred from the site of plume formation to the ICP in a process that allows each separate sample plume to be distinctly analyzed. The plume is transported from the zone of formation to the ICP through, at least in part, a conduit or injector tube ("injector"). The tube may be formed, for example, by drilling through a suitable material to produce a lumen (e.g., a lumen with a circular, rectangular or other cross-section) for transit of the plume. An injector tube sometimes has an inner diameter in the range 0.2 mm to 3 mm. In some embodiments the injector conduit has a smaller diameter, for example when incorporated with or into a microfluidic device. In some embodiments, the inner diameter of the injector varies along the length of the injector. For example, the injector may be tapered at an end. An injector sometimes has a length in the range of 1 centimeter to 100 centimeters. In some embodiments the length is no more than 10 centimeters (e.g., 1-10 centimeters), no more than 5 centimeters (e.g., 1-5 centimeters), or no more than 3 cm (e.g., 0.1-3 centimeters). The injector may be formed, without limitation, from metal (e.g., steel), quartz, glass, sapphire or other materials. In some embodiments the injector lumen is straight along the entire distance, or nearly the entire distance, from the ablation source to the ICP. In some embodiments the injector lumen is not straight for the entire distance and changes orientation. For example, the conduit may make a gradual 90 degree turn. This configuration allows for the plume to move in a vertical plane initially while the axis at injector inlet will be pointing straight up, and move horizontally as it approached the ICP torch (which is commonly oriented horizontally to take advantage of convectional cooling). In some embodiments the injector is straight for a distance of at least 0.1 centimeters, at least 0.5 centimeters or at least 1 centimeter from the aperture though which the plume enters or is formed.

As used herein, the "centerline" of an injector lumen is an imaginary line through the center of, and extending out of, the lumen, optionally a line following an axis of symmetry, and is a useful reference for orientation. For example, a laser beam, the orientation of plume expansion, and centerline may be aligned with each other. In another example, the orientation of plume expansion may be transverse (e.g., orthogonal) relative to the centerline.

In accordance with the present teachings, each separate sample plume can be distinctly analyzed by the mass analyzer. In one aspect, the device is configured so that spreading of the plume in ablation cell (ablation source) and injector is smaller than the spreading that occurs in the ICP source and the mass analyzer. In one aspect, plumes may be distinctly analyzed by transferring each ablated plume to the ICP in a time period that is within the cumulative transit time of the plume to the ICP and ion detection by the mass analyzer. This can be accomplished by capturing each sample plume through a gas flow and under a transfer configuration such that the ratio between the plume broadening during transfer time period (i.e., transfer of the ablation plume from the site of ablation to the plasma) and the broadening during ion transit time period (i.e., transfer of ions from the plasma to the mass analyzer) is equal to or less than one.

Generally, the sample particle size limit for which an ICP ion source can effectively vaporize and ionize for the purpose of analytical detection is in the order of about 10 µm or less. Particles produced by the laser ablation at 1 micrometer scale are below 1 micrometer and are well suited for ICP ion source. For discrete particles analysis (such as may be carried out using CyTOF® instrumentation, Fluidigm Canada Inc.), the typical rate at which these particles can be ionized and analytically detected can be a function of the cumulative broadening or spread of transit time of the sample in the plasma while the particles are being evaporated and ionized and of the ions' transit time broadening or spread between the ICP and its detection by the mass analyzer. Generally the cumulative time broadening or spread can be of the order of about 200 µs duration. Consequently, for particles of 10 µm or less that are spatially separated, analyzing each distinct particle can be achieved by transferring each particle to the ICP in a time period of the order of 200 µs. In some embodiments the particles are transferred to the ICP in less than 200 µs, or less than 150 µs. Accordingly, in a sample introduction system where imaging of biological samples can be performed by laser ablation, a laser system can be configured to operate with sufficiently focused laser pulses to ablate a sample area in the order of about 1 µm, such as the application of a femtosecond pulsed laser for example. With this configuration, the ablated plumes formed by each laser pulse can include sample particulates with dimensions typically about 1 µm or less. Under certain conditions as described herein, these particulates can be captured and transferred to meet the transfer time period as required and, subsequently, each distinct plume can be effectively vaporized and ionized by the ICP.

Additionally, while operating the laser with continuous series of pulses such as in the case of rasterizing across a sample surface for two dimensional imaging, the distinctiveness of each plume and the spatial separation between each subsequent plume can be maintained between the plume's zone of formation and the point of vaporization and ionization in the ICP ion source. For example, as a plume is carried through a conduit, such as the injector tube shown in FIG. 1, the particles in the plume can spread and expand outwardly in a radial direction before it enters the plasma of the ICP. Spreading of the particles produced in the plume can depend on its diffusion coefficient, the velocity profile of carrier flow and the distribution of particle density as it is formed and as it evolves during transit to the ICP. For example, the femtosecond laser ablation spot size of 1 μm can produce a plume with an initial cross section diameter of about 100 μm or less before further spreading during its transit. The extent of spreading of the plume can also be a function of the dimension of the ablated particle; larger particles tend to have lower diffusion spreading but with higher momentum resulting in potential losses due to contacting the inner walls of the injector tube. It is thus desirous to minimize the plume spreading and/or to transfer the plume to the ICP within sufficient time to vaporize and ionize before the extent of spreading presents any challenging effects.

Accordingly, in various embodiments, the use of a laser for ablating 1 μm sample spots and efficiently transporting the plume so that the spreading is maintained within the internal diameter of the injector tube can be achieved by the exemplary arrangements described herein and in the accompanying drawings.

For a given laser ablation system and given sample, ablated plumes expand after the laser ablation until they reach a characteristic volume, referred to as the "sampling volume." It is desirable to configure the system to minimize the sampling volume, and to increase the velocity with which the gas flow carries the plume away from the sampling volume. The combination of a small sampling volume and fast gas flow reduces the time spreading of the plume transfer into the injector. The sampling volume can be described by the envelope of the plume at the moment when the velocity of plume expansion in any of the dimensions falls substantially (~10 times) below the sonic velocity of the surrounding gas media. Without limitation, exemplary sampling volumes may be in the rang $10^{-6}$ mm$^3$-10 mm$^3$. Often the sampling volume is in the range 0.001 mm$^3$-1 mm$^3$. The capture flow, where present, flows into at least part of the sampling volume and carries at least a portion of the plume into the injector whereupon it may be transported by the transfer flow to the IPC. It is desirable that the velocity of capture flow when it enters the sampling volume be substantial (e.g., >1 m/s, >10 m/s, >100 m/s, or >500 m/s). In some embodiments the velocity of capture flow when it enters the sampling volume can be estimated by measuring the velocity of the capture flow into the injector (e.g., though the injector aperture). In some embodiments this measured velocity is >1 m/s, >10 m/s, >100 m/s, or >500 m/s. In contrast to the present invention, if the plume is not swept away rapidly, it will continue to expand and diffuse, undesirably filling the entire ablation cell.

In one aspect In one aspect, the invention provides a laser ablation configuration in which the laser beam is directed to a target. In one embodiment, the target comprises a substrate and a sample disposed on the substrate. In one embodiment the substrate is transparent and the target is a transparent target.

In one aspect, the invention provides a laser ablation configuration (discussed below in the context of, but not limited to, FIG. 2), for "through-target" ablation. In this configuration, the pulse of a laser beam is directed through the transparent target and a sample plume (the "ablated plume" or the "plume") is formed downstream of the beam into an injector. Also see FIGS. 3-5. Through-target illumination is advantageous for optimizing transit time broadening due to the removal of optical elements (windows, objective lenses, etc.) from the straight path of the plume. In one aspect, the invention provides a laser ablation system comprising (a) a laser capable of producing laser illumination; (b) a laser ablation cell (or laser ablation source) into which a transparent target may be introduced and an injector with an opening through which an ablated plume may enter, where the laser illumination originates from a surface on one side of the transparent target and the injector opening is on the other side. Other features that may be included in the system are described throughout this disclosure including the examples.

In FIG. 1, a laser ablation mass cytometer comprises a laser ablation source that can be connected to an injector, such as a tube fabricated from quartz or other generally suitable material, and mounted for sample delivery into an inductively coupled plasma (ICP) source, also referred to as an ICP torch. The plasma of the ICP torch can vaporize and ionize the sample to form ions that can be received by a mass analyzer.

Figure 2:
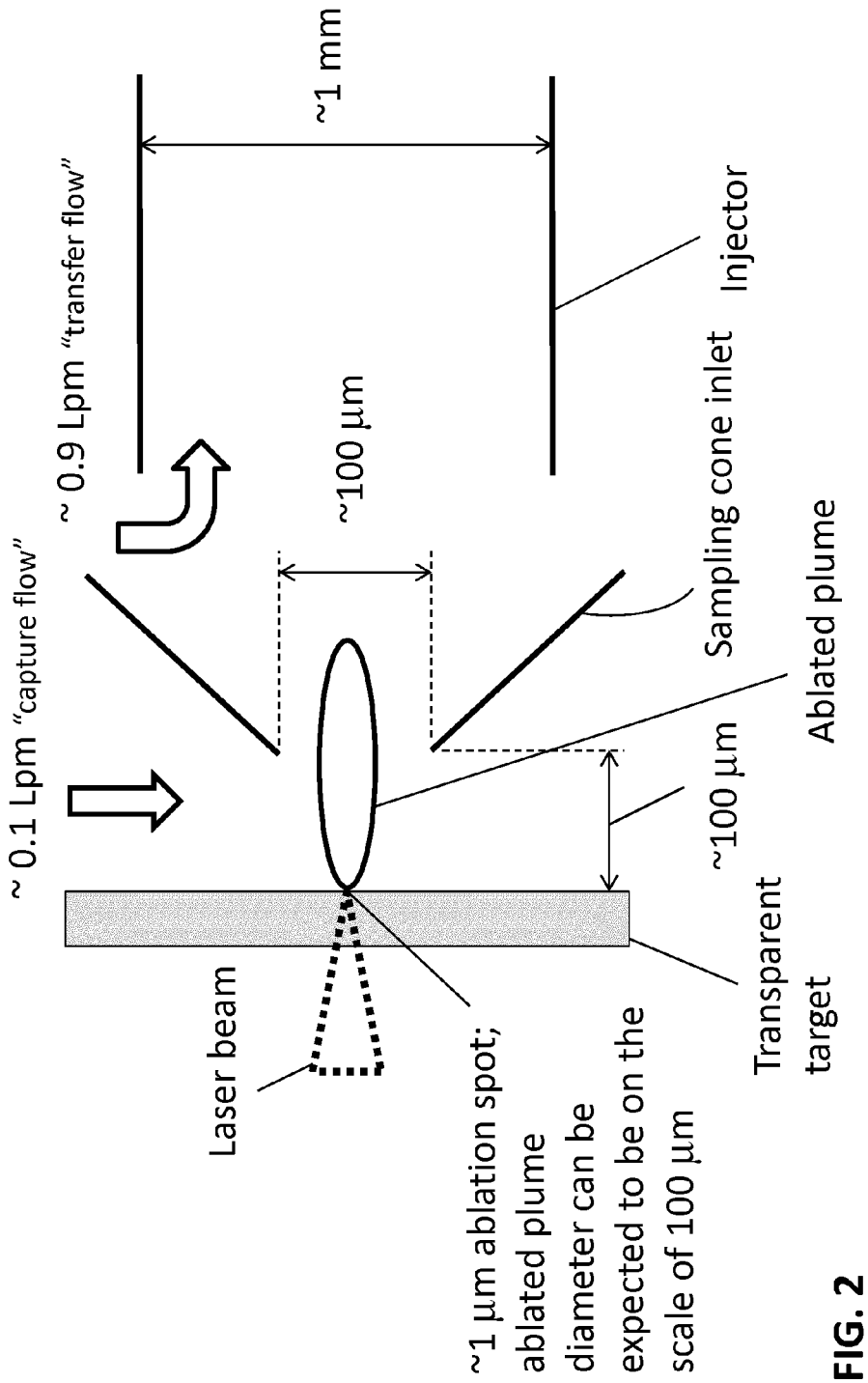
FIG. 2 is a diagrammatic view of an embodiment of the laser ablation source of FIG. 1 showing the sampling of the laser ablated plume through an aperture configured for transferring the plume into an injector.

In various embodiments according to FIG. 2, the sample of interest can be configured for laser ablation by using a sample formatted to be compatible with a transparent target. A sample can be placed onto a transparent substrate, incorporated into a transparent substrate or can be formed as the transparent target. Suitable laser-transparent substrates may comprise glass, plastic, quartz and other materials. Generally the substrate is substantially planar or flat. In some embodiments the substrate is curved. Substrates are from 0.1 mm up to 3 mm thick, in certain embodiments. In some embodiments, the substrate is encoded (see, e.g., Antonov, A. and Bandura, D., 2012, U.S. Pat. Pub. 2012/0061561, incorporated by reference herein). In this configuration, the pulse of a laser beam is directed through the transparent target and a sample plume (the "ablated plume" or the "plume") is formed downstream of the beam into an injector.

The injector, or injector tube, can have an inlet configured to capture the ablated plume; such as the inlet formed as a sample cone having a small opening or aperture as illustrated in FIG. 2. In this configuration, the sample cone can be positioned near the area, or zone, where the plume is formed. For example, the opening of the sample cone may be positioned from 10 μm to 1000 μm from the transparent target, such as about 100 μm away from the transparent target. Consequently, the ablated plume can be generated and formed at least partially within the expanding region of the cone. In some embodiments, the diameter of the aperture and/or dimensions of the spacing (including angles) are adjustable to permit optimization under various conditions. For example, with a plume having a cross sectional diameter in the scale of 100 μm, the diameter of the aperture can be sized in the order of 100 μm with sufficient clearance to prevent perturbation to the plume as it passes.

The injector can continue downstream of the sampling cone for receiving the ablated plume in such a configuration as to encourage the movement of the plume and preserve the spatial distinctiveness of each subsequent plume as a function of the laser pulses. Accordingly, a flow of gas can be introduced to aid in directing the plume through the aperture of the sampling cone in order to capture (capture flow) each plume distinctively while an additional flow of gas can be introduced to the injector for transferring (transfer flow or sheath flow) each distinctly captured plume towards the ICP. Another function of the transfer or sheath flow is to prevent the particles produced in the plume from contacting the walls of the injector. The gas(es) may be, for example, and without limitation, argon, xenon, helium, nitrogen, or mixtures of these. In some embodiments the gas is argon. The capture flow gas and the transfer flow gas may be the same or different.

It is within the ability of one of ordinary skill in this field guided by this disclosure to select or determine gas flow rates suitable for the present invention. The total flow through the injector is typically dictated by the requirements of the ICP ionization source. The laser ablation setup needs to provide the flow that would match these requirements. For example, in FIG. 2, as well as other figures illustrating various configurations, the injector tube has been generally described with a 1 mm inner diameter in conjunction with the cumulative gas flow rate of about 1 liter per minute (0.1 liter per minute capture flow plus 0.9 liter per minute transfer flow). It would be expected that smaller or larger diameter injectors, along with the correspondingly selected gas flow rates, can be applied to the various geometries presented with similar expected results. Conditions for maintaining non-turbulent gas dynamic within the injector tube in order for preserving the distinctiveness of each separate ablated plume are desirable.

As described herein, given a particular configuration of elements (e.g., a particular configuration of gas inlet positions, apertures, injector properties, and other elements), the capture and transfer flow rates are selected to result in transfer of each ablated plume to the ICP in a time period that is within the cumulative transit time of the plume between the ICP and its detection by the mass analyzer. This can be accomplished by capturing each sample plume through a gas flow and under a transfer configuration such that the ratio between the plume broadening during transfer time period and the broadening during ion transit time period is equal to or less than one. That is, the time broadening (or time spreading) of the transit signal that is important. ICP-MS devices (such as the CyTOF® ICP-TOF instrument, Fluidigm Canada Inc.) are characterized by an inherent broadening of the signal. In the case of laser ablation, the act of injecting a single plume may or may not be fast in comparison to the time spreading on the ICP-MS itself. The spreading of the plume before plasma depends on the design of the ablation cell and plume delivery channel (injector). It is desirable that the laser ablation cell and its sample delivery system (injector) does not spread the original ablation plume more than the inherent broadening of the remaining instrument. This condition ensures that the spike in detection signal produced by ablation plume is as sharp (in time) as it could be for the chosen instrument. If the spreading of the plume is much longer then the spreading in the ICP-MS, an event of laser ablation from a single pulse will come out much broader at the detector. But, if the spreading in the laser ablation section is smaller than the instrument spreading the total spreading will be dominated by the instrument spreading. Thus, one can measure the instrument spreading using calibration beads and then measure the total spreading from a single laser pulse and compare these two numbers. If the spreading from the laser ablation is smaller than the spreading from the instrument, the total spreading will be less than 2-times of the instrument spreading.

The characteristic instrument time broadening can be measured experimentally, for example using labeled cells or calibration beads. Any time a single bead enters a mass cytometer (e.g., CyTOF® ICP-TOF instrument) the bead goes through evaporation and ionization in plasma and then goes through the mass analyzer until its signal reaches detector. The transient event is detected and used to record information about the particular bead, such as the width of the transient signal (which represents the time spread from a single event) and the value of spreading that occurs starting from the ICP source and ending at the detector.

In some embodiments, the device is configured to allow time spreading of between 10 and 1000 microseconds for the path defined between the sample and the ion detector of the mass analyzer.

Typical capture flow rates are in the range of 0.1 to 1 Lpm. An optimal capture flow rate can be determined experimentally, but is usually at the lower end of the range (e.g., about 0.1 Lpm). Typical transfer flow rates are in the range of 0.1 to 1 Lpm. An optimal transfer flow rate can be determined experimentally, but is usually at the higher end of the range (e.g., about 0.9 Lpm). In some embodiments, the capture flow rate is lower than the transfer flow rate. The transfer flow rate can be 0 in some cases, for example if the capture flow rate is approximately 1 Lpm. Often the transfer flow rate is in the range of 0.4-1 Lpm (e.g., 0.4, 0.6, 0.8 or 1 Lpm).

For illustration, in the configuration shown in FIG. 2, the flow rate of the gas supplied for capturing the plume through the sampling cone can be about 0.1 liters per minute while the transfer flow of about 0.9 liters per minute can pass through a 1 mm inner diameter injector tube. The gas flows and their introduction orientation can be optimized for effective capture and transfer of each ablated plume so that each plume maintains its distinctiveness.

Figure 3:
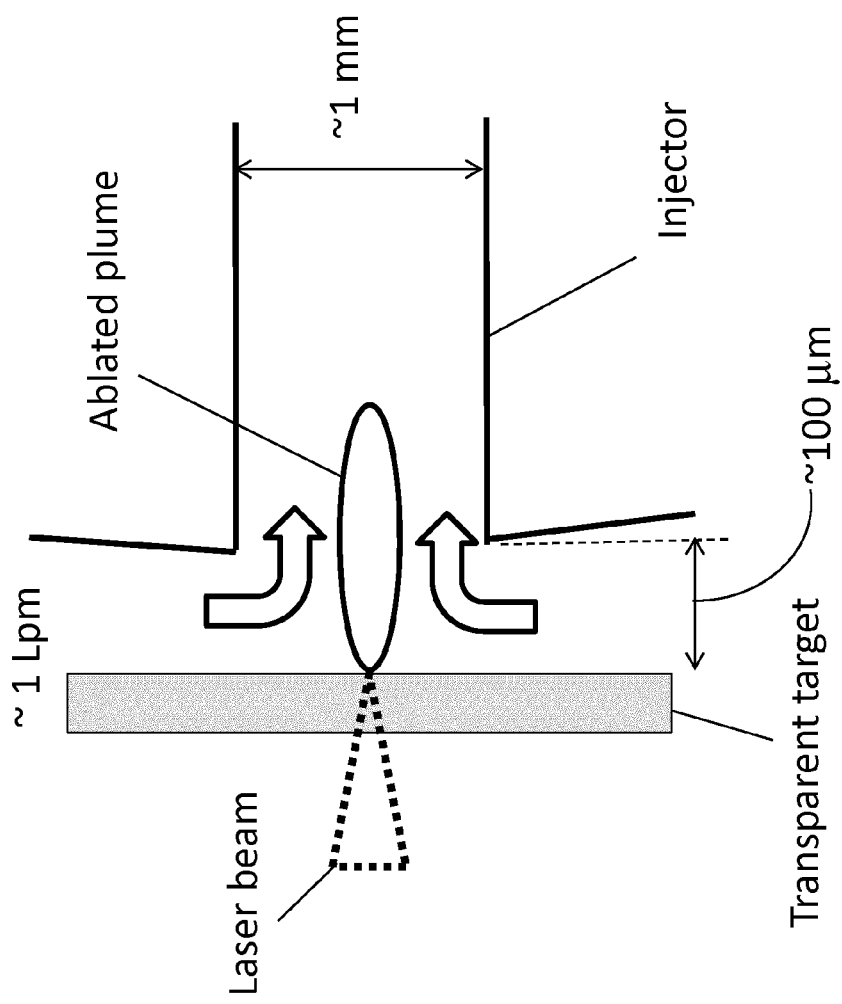
FIG. 3 is a view of an alternative configuration similar to FIG. 2 with the plume sampled directly into the injector.

In various embodiments according to FIG. 3, the sampling cone of FIG. 2 can be omitted so that an open ended injector can be positioned in place of the aperture. In this configuration the accumulative flow rate of about 1 liter per minute of the supply gas can be introduced in such a way as to be able to capture and to transfer each ablated plume distinctly and directly into the injector. In some embodiments the distance between the surface of the transparent target and the injector inlet is 500 µm or less, such as less than about 200 µm, less than about 100 µm or less than about 50 µm. In the configuration of FIG. 3, there is no separate capture flow and transfer flow. Instead, a single gas flow directs the plume through the aperture and transfers the distinctly captured plume towards the ICP. In this arrangement, the gas flow is often in the range of 0.2 liters per minute to 2 liters per minute.

Figure 4:
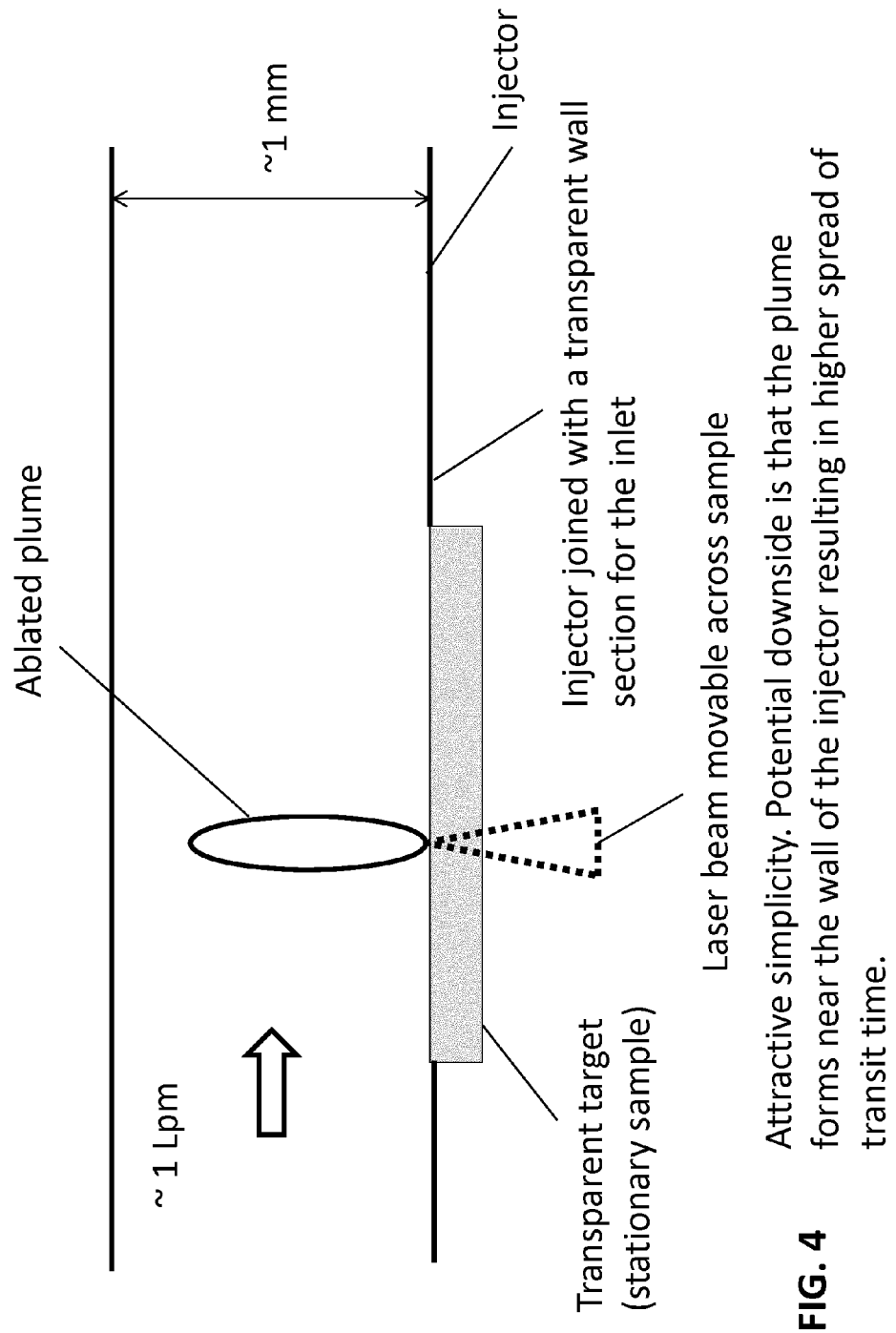
FIG. 4 and FIG. 5 are diagrammatic views of further various embodiments of the laser ablation source of FIG. 1 showing the generation and the sampling of the laser ablated plume within the injector.
Figure 5:
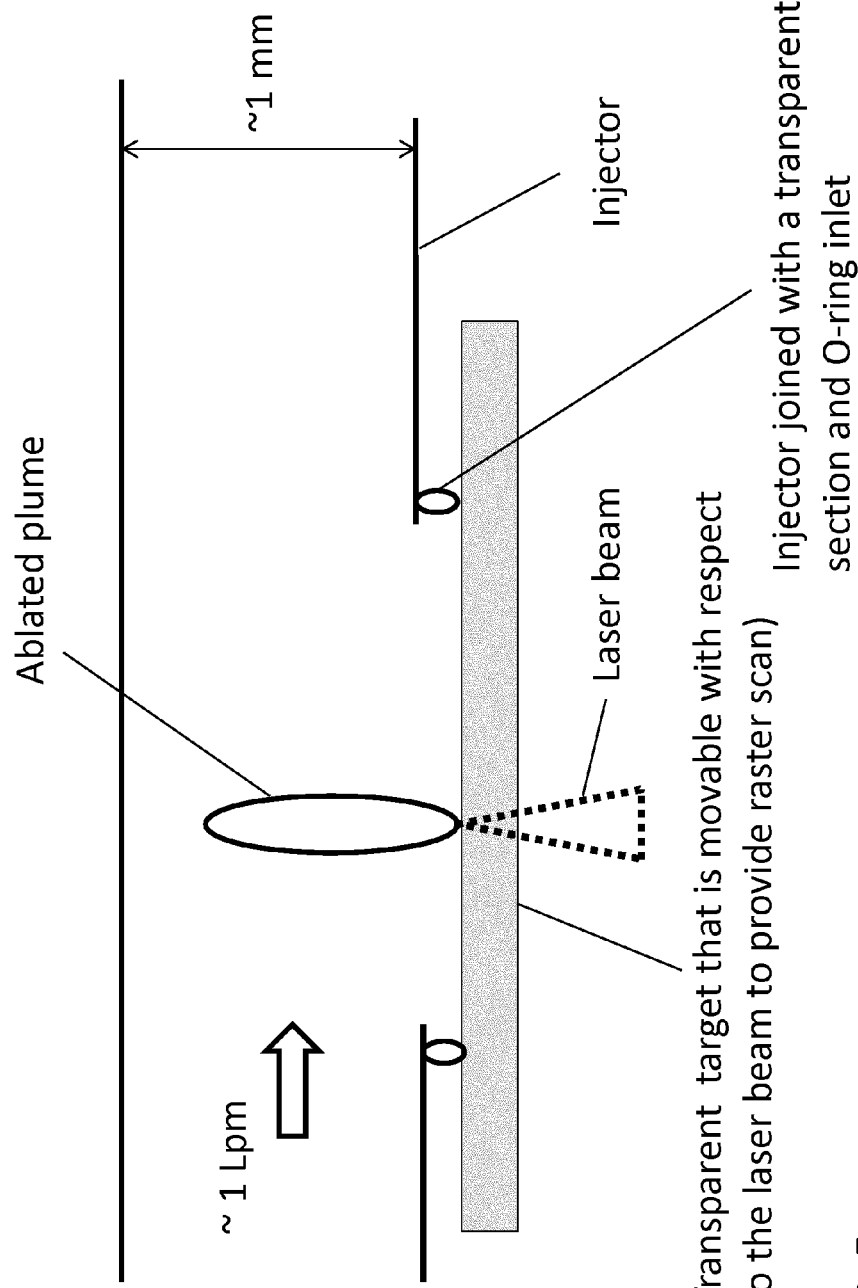

In various embodiments, the ablated plume can be formed directly within the injector tube with its direction of formation oriented in the transverse direction as indicated in FIG. 4 and FIG. 5. With the similar transparent target configuration as described according to FIG. 2, each ablated plume can be captured by the gas flow (about 1 liter per minute) and drawn downstream to the ICP. Since the transparent target illustrated in FIG. 4 is in a fixed position with respect to the injector tube, the location of each ablation spot can be varied to provide scanning capabilities. For example, the incident laser beam ablation can be moved to various spots of interest across the stationary sample or moved in a raster pattern to provide greater imaging capability. Generally in raster operation, the pulsed laser operates continuously as the location of ablation changes according to a set pattern. Alternatively, in various embodiments, the laser beam can remain stationary while the target can be configured for movement to provide different spots for the ablation as illustrated in FIG. 5.

Figure 6:
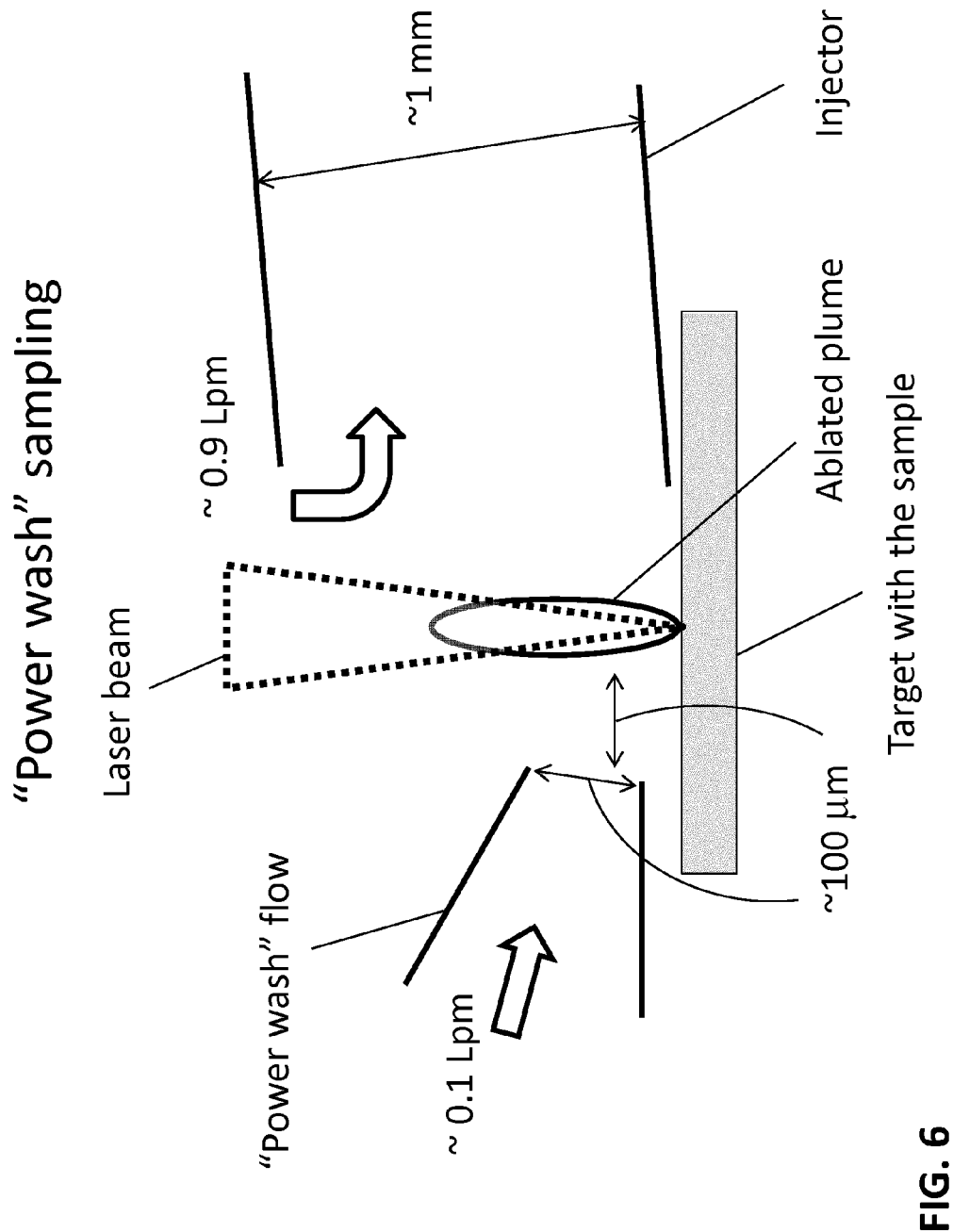
FIG. 6 is a view of an alternative configuration similar to FIG. 2 but showing a 'power wash' flow directed normal to the plume formation to direct the plume for transfer into the injector.

In various embodiments according to FIG. 6, the laser beam can be directed incident onto the target from the same side as the sample. In this instance, the sample can be placed on a substrate and each pulse of the laser beam can generate the ablated plume expanding in the direction of the incident laser. The laser light might be about orthogonal to the substrate or may be oriented at other angles, which will result in ablation spot that is stretched (for instance, elliptical instead of round). A constrain to the laser light angle is that the light itself converges in a cone. Focusing of the beam to 1 micrometer scale requires the cone angle to be quite wide (often expressed as operating at high numerical aperture). This means that significant tilting of the laser beam might affect the ability to focus the laser to a tight spot.

FIG. 6 illustrates the use of a "power wash." A 'power wash' flow of gas can be directed near (e.g., at about 100 μm distance away) the zone from which the plume is formed. The gas flow from the 'power wash' can force the ablated plume, or redirect the plume, towards the inlet end of the injector tube, effectively capturing each plume as it is formed or generated. With the similar configuration as described according to the above examples, the injector tube can be provided with a gas flow (about 0.9 liters per minute in this illustration) to capture and transfer the plume towards the ICP. In various embodiments for example, the 'power wash' flow can be achieved with a flow of gas (about 0.1 liter per minute) delivered. through a narrow nozzle (about 100 μm in diameter for example) for creating a gas jet suitable for redirecting each subsequent ablated plume into the injector tube. The source of the power wash gas flow (e.g., nozzle) can be referred to as a "gas inlet," because it is an inlet of the power wash gas flow toward the plume. Alternatively the source of the power wash gas flow can be referred to as a "port." For example, the 'power wash' flow of gas can emerge from a nozzle at a distance of 50 μm to 200 μm from the laser ablation spot (the zone of formation of the plume). It will be clear that, as used in this context, "nozzle" does not refer to any particular structure, but refers to the outlet from which the power wash gas emerges. As illustrated in FIG. 6, the diameter of the power wash nozzle is smaller than the inner diameter (or equivalent cross-sectional dimension) of the injector. For example, the diameter of the nozzle may be from 10% to 50% of the diameter of the injector. In some embodiments the power wash directs the plume into a cone-shaped injector inlet.

Figure 7:
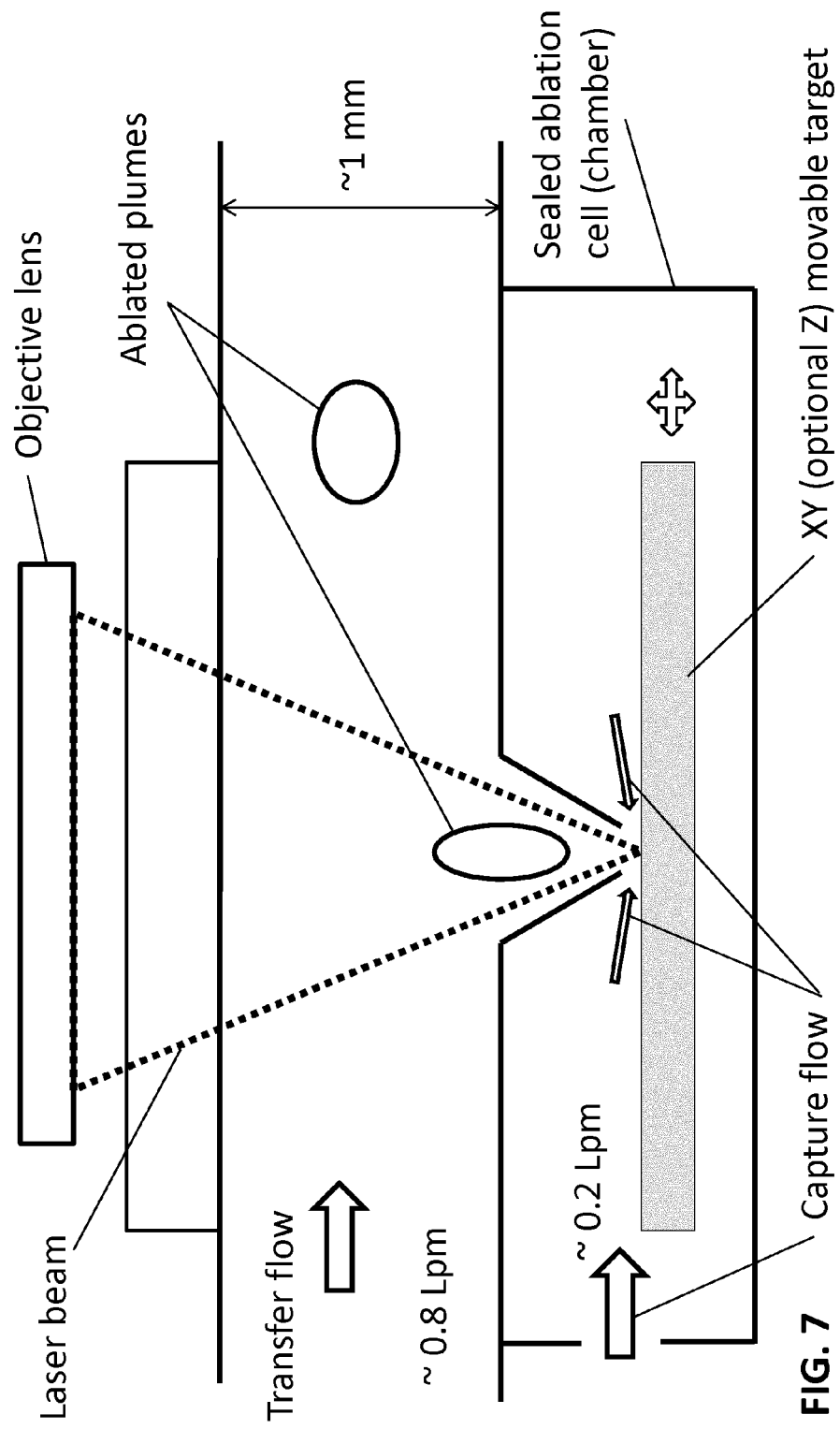
FIG. 7 shows an embodiment where the sample under study is illuminated by the laser light from the top side.

FIG. 7 shows an embodiment where the sample under study is illuminated by the laser light from the top side. The laser light is focused by an objective then passes through an optical window and finally enters sealed ablation chamber through a conical conduit. The conical shape of the conduit allows for the laser light to pass to the target while providing a conduit for the capture gas to exit the chamber. The capture gas carries the content of ablation plume and then merges with the sheath flow. By choosing dimensions of the gas channels and flow rates one can ensure that the capture flow gets surrounded by the sheath flow and that the plug from an ablation plume stays near the axis of the injector flow. This location of the plume facilitates the fastest transfer of the plume with reduced time spreading.

Figure 8:
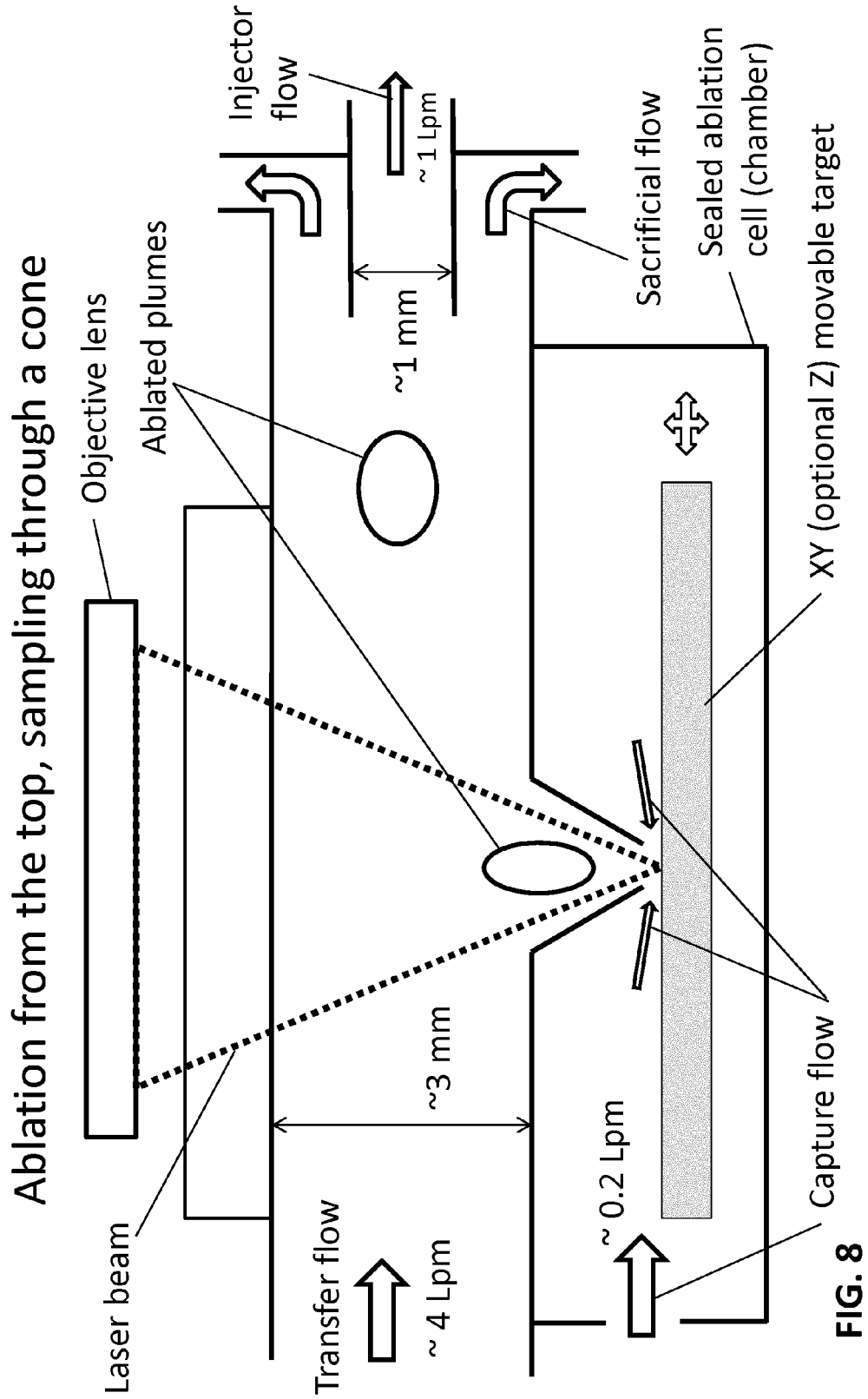
FIG. 8 shows an embodiment in which a part of the sheath flow is discarded as a sacrificial flow while the core of the sheath flow containing capture flow and plume material enters.

FIG. 8 shows a configuration similar to that of FIG. 7 and illustrates that a stronger sheath flow may be used to surround flow with plume material in the center of the flow. FIG. 8 illustrates that a part of the sheath flow is discarded as a sacrificial flow while the core of the sheath flow containing capture flow and plume material enters a short conduit that supplies this flow into the ICP.

The technique of utilizing sacrificial flow illustrated in FIG. 8 can be applied to other configurations described above. In such embodiments the injector can be considered to have two portions with different inner diameters. A major benefit of sacrificial flow configuration is that the capture flow and the plume material stay near the center of the tubing where velocity profile of the gas flow is nearly flat, i.e. different parts of the captured plume advance with similar velocities.

Figure 9:
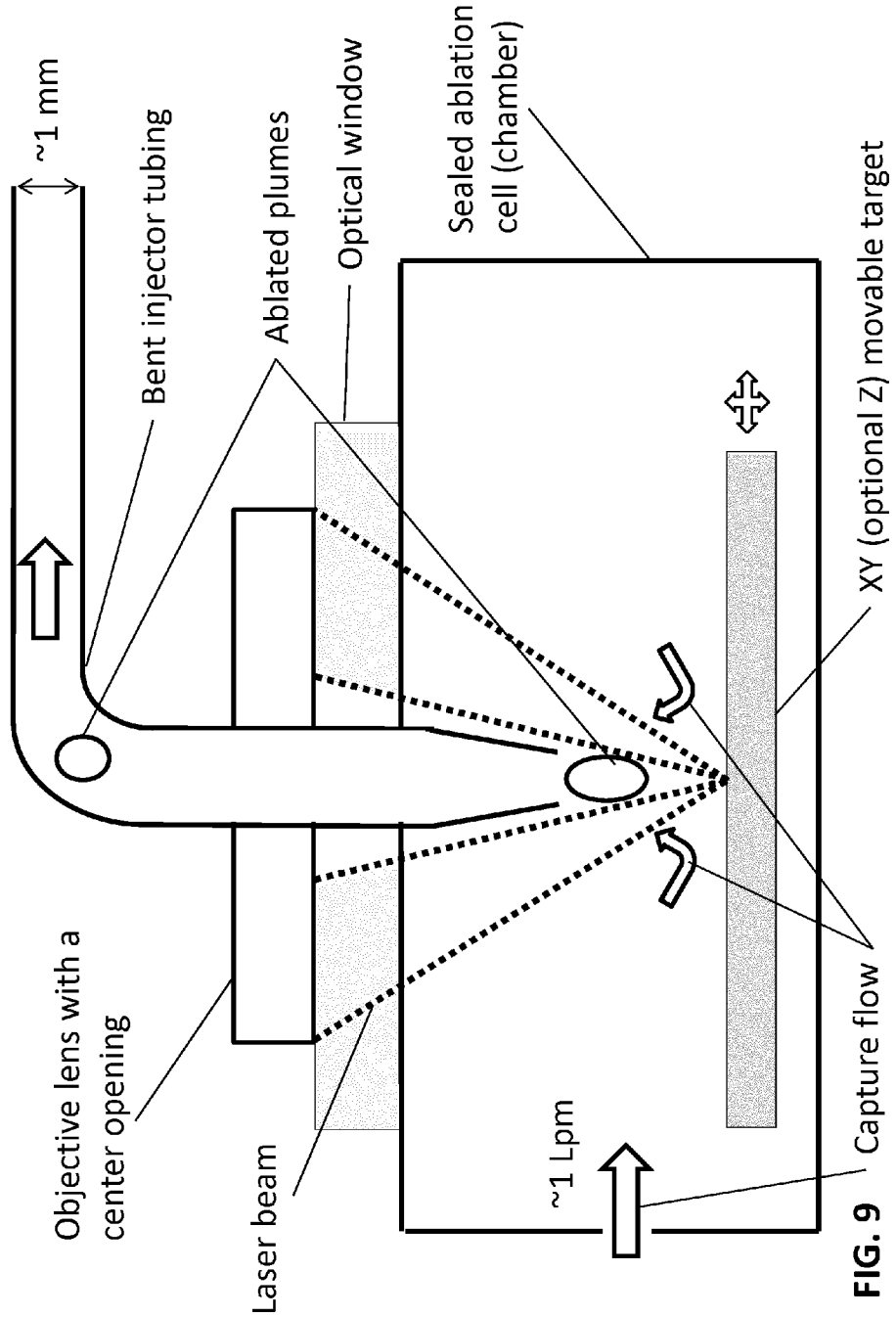
FIG. 9 shows an arrangement in which the plume is sampled into an injector that passes through the objective lens.

FIG. 9 shows another embodiment with laser beam illumination on top of the sample. Here the plume is sampled into the sampling conduit arranged about normal to the target. The plume material is surrounded by the capture flow that also acts as a sheath flow. The gas dynamics of the capture of the plume in FIG. 9 resembles that of FIG. 3 where through-target illumination is used. Since the laser light in FIG. 9 is also positioned normal to the target (as is the gas conduit) the objective lens and the optical window have an opening for the gas conduit. After passing through the objective lens the conduit is bent to take the sample away from the optical path and move it into the ICP ion source.

Figure 10:
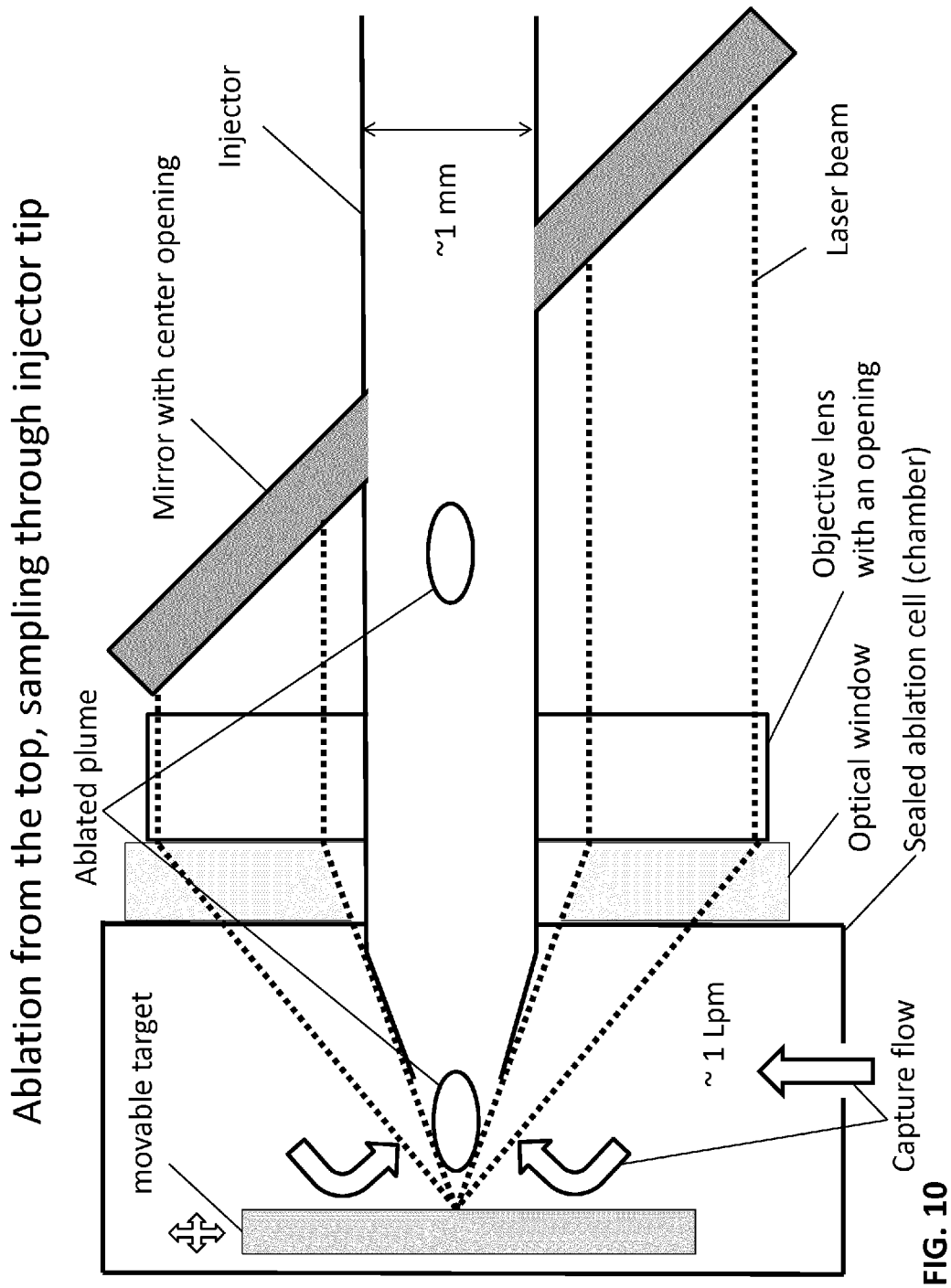
FIG. 10 shows an arrangement in which the plume is sampled into an injector that passes through the objective lens and a mirror.

FIG. 10 shows an arrangement in which laser ablation and plume sampling is similar to the embodiment shown in FIG. 9. However, to avoid bending the gas conduit further downstream the laser light is bent instead using a mirror. Here the optical window, the objective length and the mirror all have openings for the passing of gas conduit carrying capture gas and plume material.

While the present teachings are described in conjunction with various embodiments, it is not intended that the present teachings be limited to such embodiments. On the contrary, the present teachings encompass various alternatives, modifications, and equivalents, as will be appreciated by those of skill in the art. For example, in the various examples illustrated in the figures, the injector tube has been generally described with a 1 mm inner diameter in conjunction with the cumulative gas flow rate of about 1 liter per minute (0.1 plus 0.9 liter per minute). It would be expected that smaller or larger diameter injectors, along with the correspondingly selected gas flow rates, can be applied to the various geometries presented with similar expected results. However, conditions for maintaining non-turbulent or nearly non-turbulent gas dynamic within the injector tube in order for preserving the distinctiveness of each separate ablated plume may be desirable.

Furthermore, in some instances of elevated laser pulse rates, more than one ablated plume can be distinctly captured and transferred to the ICP within the cumulative transit time spread as discussed above. For example, at a repetition rate of 10 kHz a pulsed laser can generate two ablated plumes in 200 μs that can be subsequently transferred to the ICP for ionization. The ions generated from the two discrete plumes can be analyzed as a single discrete packet of ions by the mass analyzer. Consequently, while the laser remains at the same ablation spot or while the laser's rate of movement over a trace of continuous spots is less than the repetition rate, the ablated plumes, and the subsequent ions, can provide an accumulative mass analysis at the same ablation spot or provide an average mass distribution along the trace respectively. It should be noted that laser repetition rate as high as several MHz can be employed resulting in a signal that represents averaging of many laser pulses. The laser can also be fired in bursts to provide a gap in the data flow between individual sampling locations (or pixels).

It will be understood that the methods and devices of the invention may be used with any of a variety of types of samples, e.g., biological samples. In one approach the sample is cellular material, such as a tissue section, cell monolayer, cell preparation, or the like. A sample may be a thinly sectioned biological tissue up to 100 micrometers thickness, a tissue sample in the order of millimeters thickness, or an un-sectioned tissue sample. In one example, thin tissue sections (such as paraffin embedded sections) may be used. For illustration, some tissue sections have a thickness of 10 nanometers to –10 micrometers. In some cases, the sample is a group of cells, or one or more selected cells from a group of cells. See, e.g., Antonov, A. and Bandura, D., 2012, U.S. Pat. Pub. 2012/0061561, incorporated by reference herein.

In some embodiments, the biological material is tagged with elemental tags, for example as described in U.S. Pat. Pub. US2010/0144056, incorporated herein by reference. A biological sample containing cells, proteins, cellular materials, of interest can be labeled with one, or several different, metal conjugated antibodies.

While the foregoing invention has been described in some detail for purposes of clarity and understanding, it will be appreciated by those skilled in the relevant arts, once they have been made familiar with this disclosure, that various changes in form and detail can be made without departing from the true scope of the invention in the appended claims. The invention is therefore not to be limited to the exact components or details of methodology or construction set forth above. Except to the extent necessary or inherent in the processes themselves, no particular order to steps or stages of methods or processes described in this disclosure, including the Figures, is intended or implied. In many cases the order of process steps may be varied without changing the purpose, effect, or import of the methods described. All publications and patent documents cited herein are incorporated herein by reference as if each such publication or document was specifically and individually indicated to be incorporated herein by reference. Citation of publications and patent documents (patents, published patent applications, and unpublished patent applications) is not intended as an admission that any such document is pertinent prior art, nor does it constitute any admission as to the contents or date of the same.

What is claimed is:

1. A method of laser ablation mass cytometry analysis using a laser ablation mass cytometer, the method comprising:
   directing pulses of a laser beam to a plurality of sites of a sample for generating an ablated plume of sample for each of the pulses;
   capturing each ablated plume;
   transferring each of the captured ablated plumes into an inductively coupled plasma (ICP); and
   ionizing each of the captured and transferred ablated plumes in the ICP, thereby generating ions for mass cytometry analysis;
   wherein the laser ablation mass cytometer comprises an injector adapted to transfer the ablated plumes to the ICP, the injector having an injector inlet positioned within a laser ablation source, the injector inlet being configured for capturing the ablated plumes;
   wherein the injector inlet forms a sample cone, wherein a narrower portion of the sample cone is an aperture of the injector inlet; wherein the sample cone is positioned adjacent an area where the ablated plume is generated; and
   wherein the method further comprises introducing a capture gas flow to bring the ablated plumes into the sample cone of the injector and introducing a transfer gas flow, separate from the capture gas flow, into the injector for transferring the ablated plumes from the sample cone toward the ICP.

2. The method of claim 1, wherein the laser ablation mass cytometer further comprises:
   the laser ablation source for generating ablated plumes from the sample;
   an ICP source for producing the ICP; and
   a gas inlet coupled to the injector inlet configured to pass a gas from the gas inlet to the injector inlet for transferring the captured ablated plume into the ICP.

3. The method of claim 1, wherein the laser beam passes through the aperture.

4. The method of claim 1, wherein the laser beam is from a femtosecond laser.

5. The method of claim 1, wherein a position of the sample is changed during analysis; and wherein, during analysis, the laser beam remains stationary.

6. The method of claim 1, wherein the laser beam pulses produce 1 micron ablation spots or less.

7. The method of claim 1, wherein the injector further includes a sacrificial flow portion where part of a sheath flow surrounding plume material is discarded before the plume material is introduced into the ICP.

8. The method of claim 1, wherein a circumference of an outer surface of the sample cone decreases toward the aperture.

9. The method of claim 1, wherein the sample comprises cells.

10. The method of claim 9, further comprising labeling the sample with at least one metal conjugated antibody.

11. A laser ablation system comprising:
    a laser configured to produce laser illumination;
    a laser ablation cell for holding a sample to be analyzed; and
    an injector for carrying an ablation plume to an ICP, the injector comprising a sample cone with a narrower portion of the sample cone forming an injector opening, and
    wherein the injector comprises an inlet for introducing a transfer gas flow into the injector, and an outlet for delivering an ablation plume to ICP-MS; and
    wherein the laser ablation cell comprises an inlet for introducing a capture gas flow, separate from the transfer gas flow, into the ablation cell.

12. The system of claim 11, further comprising a transfer gas source for producing a transfer flow in the injector and a capture gas source for producing a capture gas flow in the ablation cell.

13. The system of claim 11, wherein the laser is a femtosecond pulsed laser.

14. The system of claim 11, wherein the laser is a solid state laser.

15. The system of claim 14, wherein the solid state laser is an Nd:YAG laser.

16. The system of claim 11, wherein the laser illumination is a laser beam pulse that produces an ablation spot of 1 um or less.

17. The system of claim 11, further comprising an inductively coupled plasma (ICP) torch coupled to the injector, and a mass analyzer configured to receive ions from the ICP torch.

18. The system of claim 17, wherein the mass analyzer is a time of flight mass spectrometer.

19. The system of claim 11, wherein the injector further includes a sacrificial flow portion where part of a sheath flow surrounding plume material is discarded before the plume material is introduced into the ICP.

20. The system of claim 11, wherein the laser, the laser ablation cell, and the injector are configured so that the laser illumination originates on one side of the sample and the injector opening is on an opposite side of the sample.

* * * * *